(12) United States Patent
Vaidyanathan

(10) Patent No.: US 6,797,834 B2
(45) Date of Patent: Sep. 28, 2004

(54) PHOSPHORIC ACID ISOMERIZATION OF A 5 (10), 9 (11)—DIENE STEROID TO THE CORRESPONDING 4, 9-DIENE STEROID

(75) Inventor: Rajappa Vaidyanathan, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 125 days.

(21) Appl. No.: 10/315,273

(22) Filed: Dec. 10, 2002

(65) Prior Publication Data

US 2003/0109728 A1 Jun. 12, 2003

Related U.S. Application Data

(60) Provisional application No. 60/339,620, filed on Dec. 12, 2001.

(51) Int. Cl.[7] .................................................. C07J 1/00
(52) U.S. Cl. ...................................... 552/646; 552/648
(58) Field of Search ................................ 552/646, 648

(56) References Cited

U.S. PATENT DOCUMENTS 3,052,672 A    9/1962  Nomine et al. .......... 260/239.5

OTHER PUBLICATIONS

K. K. Pivnitsky, N. N. Gaidamovich, and I. V. Torgov, "Configuration and Properties of DL–$\Delta^{4,9}$–19–Nor–D–Homoandrostadiene–14α–OL–3,17A–Dione", *Tetrahedron*, vol. 22, 1966, pp. 2837–2844.

Louis F. Fieser and Srinivasa Rajagopalan, Evelyn Wilson and Max Tishler, "The Conversion of Cholic Acid into 3α–Hydroxy–12–keto$\Delta^{9(11)}$–cholenic Acid", *Chemical Laboratory of Harvard University and the Research Laboratories of Merck & Co., Inc.*, Sep. 1951, pp. 4133–4135.

Arthur J. Birch, "Hydroaromatic Steroid Hormones. Part I. 10–Nortestosterone", *The University Chemical Laboratory*, No. 80, 1950, pp. 367–368.

Primary Examiner—Barbara P. Badio
(74) Attorney, Agent, or Firm—Thomas A. Wootton

(57) ABSTRACT

The invention is a process for the preparation of a $\Delta^{4,9}$-steroid of formula (II)

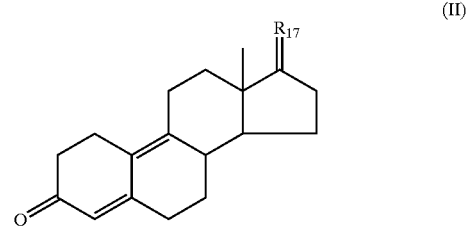

(II)

which comprises contacting a $\Delta^{5(10),9(11)}$-steroid of formula (I)

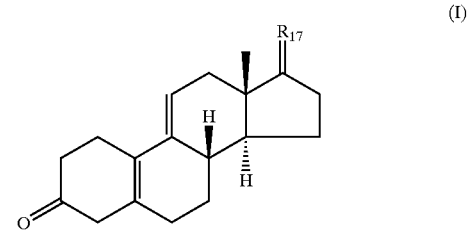

(I)

with a phosphorous containing acid.

16 Claims, No Drawings

PHOSPHORIC ACID ISOMERIZATION OF A 5 (10), 9 (11)— DIENE STEROID TO THE CORRESPONDING 4, 9-DIENE STEROID

CROSS-REFERENCE TO RELATED APPLICATIONS

This patent application claims priority of invention under 35 U.S.C. §119(e) from U.S. provisional patent application Ser. No. 60/339,620 filed Dec. 12, 2001.

BACKGROUND OF THE INVENTION

1. Field of the Invention

The present invention is a chemical process for the isomerization of the $\Delta^{5(10),9(11)}$-double bonds in a steroid to the corresponding $\Delta^{4,9}$-isomer.

2. Description of the Related Art

*J. Am. Chem. Soc.*, 73, 4133 (1951) discloses isomerization of a $\Delta^{8(9)}$-12-one steroid to the corresponding $\Delta^{9(11)}$-12-one steroid using hydrochloric acid in methanol.

*J. Chem. Soc.*, 367 (1950) discloses isomerization of $\Delta^{5(10)}$-3-one steroid to the corresponding $\Delta^{4(5)}$-3-one steroid using sodium ethoxide.

*Tetrahedron*, 22, 2837 (1966) discloses isomerization of a $\Delta^{5(10)}$-3-one steroid to the corresponding $\Delta^{4(5)}$-3-one steroid using potassium hydroxide in ethanol.

U.S. Pat. No. 3,052,672 discloses isomerization of $\Delta^{5(10),9(11)}$-3-one steroid to the corresponding $\Delta^{4(5),9(10)}$-3-one steroid using perchloric acid in acetic acid.

These documents while disclosing isomerization of double bonds leading to conjugation with the carbonyl group in six-membered rings in steroidal compounds do not use a phosphorous containing acid.

SUMMARY OF INVENTION

Disclosed is a process for the preparation of a $\Delta^{4,9}$-steroid of formula (II)

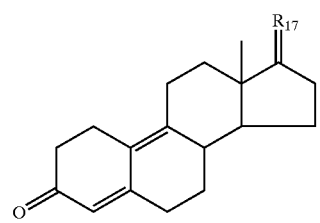

(II)

where $R_{17}$ is:

(1) =O;
(2) $\alpha$-$R_{17-1}$:$\beta$-$R_{17-2}$ where one of $R_{17-1}$ and $R_{17-2}$ is:
  (a) —OH,
  (b) —O—Si($R_{17-2a}$)$_3$ where $R_{17-2a}$ are the same or different and are $C_1$–$C_6$ alkyl or phenyl,
  (c) —O—CO—$R_{17-2b}$ where $R_{17-2b}$ is:
    (i) $C_1$–$C_6$ alkyl,
    (ii) phenyl,
  (d) —O—$R_{17-2b}$ where $R_{17-2b}$ is as defined above, and the other of $R_{17-1}$ and $R_{17-2}$ is —H; which comprises
(1) contacting a $\Delta^{5(10),9(11)}$-steroid of formula (I)

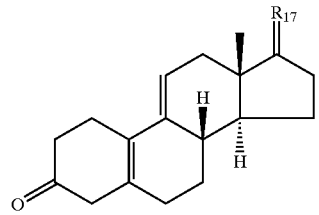

(I)

where $R_{17}$ is as defined above, with a phosphorous containing acid selected from the group consisting of phosphoric acid, polyphosphoric acid, metapahosphoric acid, pyrophosphoric acid, tripolyphosphoric acid, tetrapolyphosphoric acid, tetrametaphosphoric acid, hypophosphoric acid, orthophosphoric acid or an acid containing phosphorus which is generated in situ.

DETAILED DESCRIPTION OF THE INVENTION

17β-Hydroxyandrosta-5(10),9(11)-dien-3-one (I) is known, see *Zhongguo Yaowu Huaxue Zazhi*, 4(1), 65–67 (1994) and FR 2745291.

The process of the invention is set forth in CHART A. The general process is the transformation of the $\Delta^{5(10),9(11)}$-steroid of formula (I) to the corresponding a $\Delta^{4,9}$-steroid of formula (II). CHART A also discloses the transformation of the preferred starting material the 17β-hydroxy-$\Delta^{5(10),9(11)}$-steroid of formula (IA) to the corresponding 17β-$\Delta^{4,9}$-steroid of formula (IIA).

The process is performed by contacting the starting $\Delta^{5(10),9(11)}$-steroid of formula (I) with a phosphorous containing acid. No solvent other than the phosphorous containing acid is required. Other solvents can be added but are not required. It is preferred that the process be performed without a cosolvent.

Phosphorous containing acids include with a phosphorous containing acid selected from the group consisting of phosphoric acid, polyphosphoric acid, metapahosphoric acid, pyrophosphoric acid, tripolyphosphoric acid, tetrapolyphosphoric acid, tetrametaphosphoric acid, hypophosphoric acid, orthophosphoric acid or an acid containing phosphorus which is generated in situ. When the phosphorous containing acid is phosphoric acid it can be prepared in situ by reaction of $POCl_3$ or $P_2O_5$ and water. It can also be prepared in situ by reaction of a mineral acid and phosphate salt such as sodium or potassium phosphate or hydrogenphosphate. It is preferred that the phosphorous containing acid is phosphoric acid.

Operable concentrations of the steroid and phosphorous containing acid start from about 1 mL of phosphoric acid/g of 17β-hydroxyandrosta-5(10),9(11)-dien-3-one (I); preferred is from about 1.5 mL to about 10 mL; more preferred is about 2 to about 5 mL. More acid is not harmful, just wasteful.

The process of the invention is performed in the temperature range of from about 0 to about 50°. It is preferred that the process be performed in the temperature range of about 10 to about 40°; it is more preferred that the process be preformed at room temperature, i.e. 20–25°.

The process should be performed for a time period of about a few minutes to a few hours. It is preferred that the process be performed for a period of about 0.25 hr to about 2 hr; more preferred is about 1 hr.

When the reaction is complete, water and an organic solvent are added for work-up. There are two different ways to work-up the present reaction. One method uses a water miscible solvent such as THF or DMF. In that case water and the water miscible solvent are added to the phosphoric acid/steroid mixture and the $\Delta^{4,9}$-steroids (II) are obtained by the "water knock-out" procedure. Alternatively, a water immiscible solvent such as methylene chloride can be used. In that situation, the water immiscible solvent is added followed by the water and the $\Delta^{4,9}$-steroids (II) are obtained by an extractive work-up.

The $\Delta^{4,9}$-steroids of formula (II) are known, more particularly 17β-Hydroxyandrosta-4,9-dien-3-one (IIA) is known, see European Patent Application 683172 (1995) and Chinese patent 1087090. 17β-Hydroxyandrosta-4,9-dien-3-one (IIA) is known to be useful as an intermediate in the production of 11β-[4-(hydroxyiminomethyl)phenyl]-17β-methoxy-17α-(methoxymethyl)estra-4,9-dien-3-one. 11β-[4-(Hydroxyiminomethyl)phenyl]-17β-methoxy-17α-(methoxymethyl)estra-4,9-dien-3-one is known, see EP 0648778. Androsta-4,9-diene-3,17-dione (II) is known, see *Chinese Journal of Medicinal Chemistry*, 4(1), 65–68 (1994).

DEFINITIONS AND CONVENTIONS

The definitions and explanations below are for the terms as used throughout this entire document including both the specification and the claims.

All temperatures are in degrees Celsius.

DMF refers to dimethylformamide.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.

TMS refers to trimethylsilyl.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Phosphoric acid refers to $H_3PO_4$.

Polyphosphoric acid refers to a polymer of phosphoric acid.

Metapahosphoric acid refers to $(HPO_3)_n$

Pyrophosphoric acid also known as dipolyphosphoric acid refers to $H_4P_2O_7$.

Tripolyphosphoric acid refers to $H_5P_3O_{10}$.

Tetrapolyphosphoric acid refers to $H_6P_4O_{13}$

Tetrametaphosphoric acid refers to $H_3P_3O_9$.

Hypophosphoric acid refers to $H_4P_2O_6$.

Orthophosphoric acid refers to $H_3PO_4$.

Nordienolone refers to 17β-hydroxyandrosta-4,9-dien-3-one.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

17β-Hydroxyandrosta-4,9-dien-3-one (II)

Phosphoric acid (120 mL) is mixed with 17β-hydroxyandrosta-5(10),9(11)-dien-3-one (I, 30 g) and is stirred at 20–25° for 2 hr. The mixture is then immersed in an ice-bath, and cooled to below 10°. DMF (210 mL) and water (450 mL) are added slowly to the flask. The product precipitates and is isolated by filtration. The filter cake is washed with water (4×600 mL) and dried overnight under reduced pressure at 45° to give the title compound, CMR (CDCl$_3$)10.45, 23.40, 25.78, 27.06, 30.56, 30.77, 36.50, 37.06, 39.35, 42.83, 51.08, 81.25, 119.04, 122.07, 125.41, 146.35, 157.28 and 199.74 δ.

Example 2

17β-Hydroxyandrosta-4,9-dien-3-one (II)

Phosphoric acid (120 mL) is mixed with 17β-hydroxyandrosta-5(10),9(11)-dien-3-one (I, 30 g) and is stirred at 20–25° for 2 hr. The mixture is then immersed in an ice-bath, and cooled to below 10°. Water (210 mL) and methylene chloride (210 mL) are added, and the mixture is stirred for 15 minutes. The mixture is transferred to a separatory funnel, and the phases are separated. The aqueous phase is extracted with methylene chloride (2×250 mL). The organic phase is washed sequentially with sodium hydroxide (10%, 300 mL) and saline (300 mL), and concentrated under reduced pressure to 550 mL. Ethyl acetate (275 mL) is added, and the mixture is concentrated to half the original volume. This was repeated two more times using ethyl acetate (100 mL) each time. Iso-octane (60 mL) is added, and the flask is cooled to 0°. The crystals are isolated by filtration and dried overnight under reduced pressure at 45° to give the title compound, CMR (CDCl$_3$)10.45, 23.40, 25.61, 27.07, 30.56, 30.77, 36.50, 37.06, 39.35, 42.84, 51.08, 81.26, 119.04, 122.07, 125.42, 146.34, 157.28 and 199.75 δ.

Example 3

17β-Hydroxyandrosta-4,9-dien-3-one (II)

Following the general procedure of EXAMPLE 1 and making non-critical variations, THF (instead of DMF) and water are added to the phosphoric acid/steroid mixture. The title compound is obtained.

CHART A

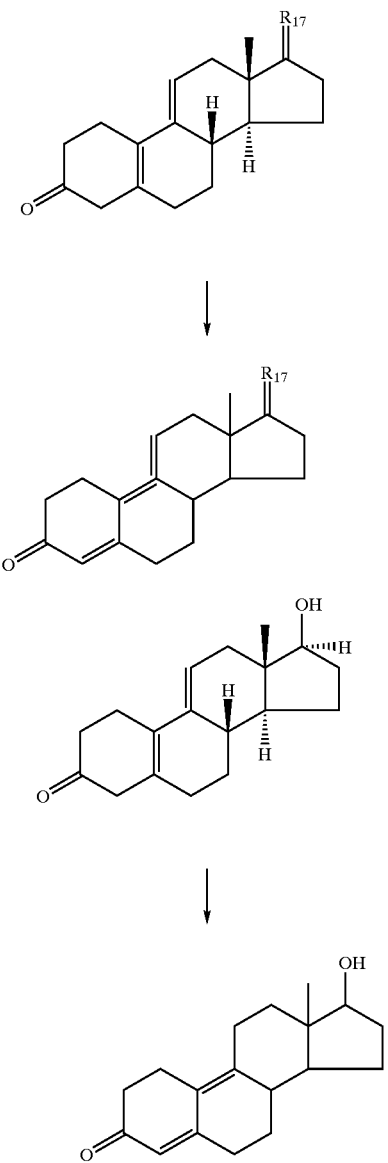

What is claimed is:

1. A process for the preparation of a $\Delta^{4,9}$-steroid of formula (II)

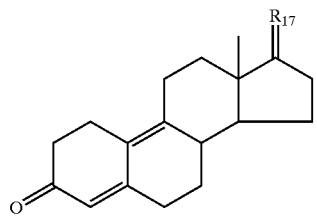

where $R_{17}$ is:
(1) =O;
(2) $\alpha$-$R_{17-1}$:$\beta$-$R_{17-2}$ where one of $R_{17-1}$ and $R_{17-2}$ is:
 (a) —OH,
 (b) —O—Si($R_{17-2a}$)$_3$ where $R_{17-2a}$ are the same or different and are $C_1$–$C_6$ alkyl or phenyl,
(c) —O—CO—$R_{17-2b}$ where $R_{17-2b}$ is:
 (i) $C_1$–$C_6$ alkyl,
 (ii) phenyl,
(d) —O—$R_{17-2b}$ where $R_{17-2b}$ is as defined above, and the other of $R_{17-1}$ and $R_{17-2}$ is —H; which comprises
(1) contacting a $\Delta^{5(10),9(11)}$-steroid of formula (I)

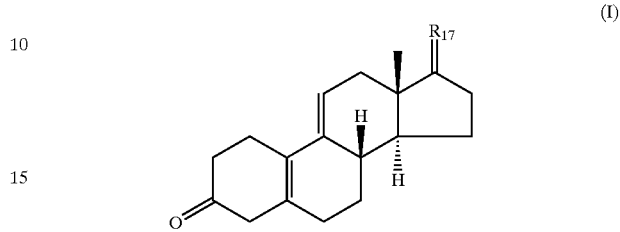

where $R_{17}$ is as defined above, with a phosphorous containing acid selected from the group consisting of phosphoric acid, polyphosphoric acid, metapahosphoric acid, pyrophosphoric acid, tripolyphosphoric acid, tetrapolyphosphoric acid, tetrametaphosphoric acid, hypophosphoric acid, orthophosphoric acid or an acid containing phosphorus which is generated in situ.

2. A process for the preparation of a $\Delta^{4,9}$-steroid of formula (II) according to claim 1 where the process was performed in a temperature range of from about 0 to about 50°.

3. A process for the preparation of a $\Delta^{4,9}$-steroid of formula (II) according to claim 2 where the process was performed in a temperature range of from about 10 to about 40°.

4. A process for the preparation of a $\Delta^{4,9}$-steroid of formula (II) according to claim 3 where the process was performed in a temperature range of from about 20 to about 25°.

5. A process according for the preparation of a $\Delta^{4,9}$-steroid of formula (II) to claim 1 where the process is performed for a period of a few minutes to a few hours.

6. A process for the preparation of a $\Delta^{4,9}$-steroid of formula (II) according to claim 5 where the process is performed for a period of about 0.25 to about 2 hr.

7. A process for the preparation of a $\Delta^{4,9}$-steroid of formula (II) according to claim 6 where the process is performed for a period of about 1 hr.

8. A process for the preparation of a $\Delta^{4,9}$-steroid of formula (II) according to claim 1 where the concentration of the reactants is from is 1 mL or more of the phosphorous containing acid/g of $\Delta^{5(10),9(11)}$-steroid (I).

9. A process for the preparation of a $\Delta^{4,9}$-steroid of formula (II) according to claim 8 where the concentration of the reactants is from about 1.5 to about 10 mL of the phosphorous containing acid/g of $\Delta^{5(10),9(11)}$-steroid (I).

10. A process for the preparation of a $\Delta^{4,9}$-steroid of formula (II) according to claim 9 where the concentration of the reactants is about 2 to about 5 mL of the phosphorous containing acid/g of $\Delta^{5(10),9(11)}$-steroid (I).

11. A process for the preparation of a $\Delta^{4,9}$-steroid of formula (II) according to claim 1 where the phosphorous containing acid is phosphoric acid.

12. A process for the preparation of a $\Delta^{4,9}$-steroid of formula (II) according to claim 1 where $R_{17}$ is =O or is $\alpha$-$R_{17-1}$:$\beta$-$R_{17-2}$ where $R_{17-1}$ is —H and $R_{17-2}$ is —OH.

13. A process for the preparation of a $\Delta^{4,9}$-steroid of formula (II) according to claim 12 where $R_{17}$ is $\alpha$-$R_{17-1}$:$\beta$-$R_{17-2}$ where $R_{17-1}$ is —H and $R_{17-2}$ is —OH.

14. A process for the preparation of a $\Delta^{4,9}$-steroid of formula (II) according to claim 1 where the phosphorous containing acid is prepared in situ.

15. A process for the preparation of a $\Delta^{4,9}$-steroid of formula (II) according to claim 14 where the phosphorous containing acid is phosphoric acid and it is prepared in situ by reaction of $POCl_3$ or $P_2O_5$ and water.

16. A process for the preparation of a $\Delta^{4,9}$-steroid of formula (II) according to claim 14 where the phosphorous containing acid is phosphoric acid and it is prepared in situ by reaction of a mineral acid and phosphate salt.

\* \* \* \* \*